US00PP32691P3

(12) United States Plant Patent
Hofmann

(10) Patent No.: US PP32,691 P3
(45) Date of Patent: Dec. 22, 2020

(54) ***CALIBRACHOA* PLANT NAMED 'INCALCOWHI'**

(50) Latin Name: ***Calibrachoa* Llave & Lex.**
Varietal Denomination: INCALCOWHI

(71) Applicant: Birgit Hofmann, Rudensheim am Rhein (DE)

(72) Inventor: Birgit Hofmann, Rudensheim am Rhein (DE)

(73) Assignee: INNOVAPLANT ZIERPFLANZEN GmbH & Co. KG, Gensingen (DE)

( * ) Notice: Subject to any disclaimer, the term of this patent is extended or adjusted under 35 U.S.C. 154(b) by 0 days.

(21) Appl. No.: 16/873,447

(22) Filed: Apr. 14, 2020

(65) Prior Publication Data

US 2020/0329608 P1 Oct. 15, 2020

(30) Foreign Application Priority Data

Apr. 15, 2019 (CA) ..... PBR 19-9760

(51) Int. Cl.
*A01H 5/02* (2018.01)
*A01H 6/82* (2018.01)

(52) U.S. Cl.
USPC ..... Plt./413
CPC ..... *A01H 6/821* (2018.05)

(58) Field of Classification Search
USPC ..... Plt./413
CPC ..... A01H 6/821
See application file for complete search history.

*Primary Examiner* — Anne Marie Grunberg
(74) *Attorney, Agent, or Firm* — C. A. Whealy

(57) ABSTRACT

A new and distinct *Calibrachoa* plant named 'INCALCOWHI', characterized by its compact and uniformly low mounding to eventually trailing plant habit; moderately vigorous growth habit; freely branching habit; dense and bushy appearance; early and freely flowering habit; large white-colored flowers; and good garden performance.

1 Drawing Sheet

Botanical designation: *Calibrachoa* Llave & Lex.
Cultivar denomination: 'INCALCOWHI'.

CROSS-REFERENCE TO A RELATED APPLICATION AND STATEMENT REGARDING PRIOR DISCLOSURES BY INVENTOR/APPLICANT

This application claims priority to a Canadian Plant Breeders' Rights application filed on Apr. 15, 2019, application number 19-9760. There have been no offers for sale anywhere in the world prior to the effective filing date of this Application and no accessibility to one of ordinary skill in the art could have been derived from the printed Plant Breeder's Rights documents.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Calibrachoa* plant, botanically known as *Calibrachoa* sp. and hereinafter referred to by the name 'INCALCOWHI'.

The new *Calibrachoa* plant is a product of a planned breeding program conducted by the Inventor in Johannesburg, South Africa. The objective of the breeding program is to create new compact, mounding and early-flowering *Calibrachoa* plants with large attractive flowers and good garden performance.

The new *Calibrachoa* plant originated from a cross-pollination conducted by the Inventor in Johannesburg, South Africa in November, 2015 of a proprietary selection of *Calibrachoa* Llave & Lex. identified as code number Ca14-5199-2, not patented, as the female, or seed, parent with a proprietary selection of *Calibrachoa* sp. identified as code number Ca14-5231-6, not patented, as the male, or pollen, parent. The new *Calibrachoa* plant was discovered and first selected by the Inventor as a single flowering plant within the progeny of the stated cross-pollination in a controlled greenhouse environment in Johannesburg, South Africa in April, 2017.

Asexual reproduction of the new *Calibrachoa* plant by vegetative terminal cuttings in a controlled greenhouse environment in Gensingen, Germany since April, 2017 has shown that the unique features of this new *Calibrachoa* plant are stable and reproduced true to type in successive generations.

SUMMARY OF THE INVENTION

Plants of the new *Calibrachoa* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'INCAL- COWHI'. These characteristics in combination distinguish 'INCALCOWHI' as a new and distinct *Calibrachoa* plant:

1. Compact and uniformly low mounding to eventually trailing plant habit.
2. Moderately vigorous growth habit.
3. Freely branching habit; dense and bushy appearance.
4. Early and freely flowering habit.
5. Large white-colored flowers.
6. Good garden performance.

The new *Calibrachoa* plant can be compared to plants of the female parent selection. Plants of the new *Calibrachoa* differ primarily from plants of the female parent selection in the following characteristics:

1. Plants of the new *Calibrachoa* are more compact than plants of the female parent selection.
2. Plants of the new *Calibrachoa* flower earlier than plants of the female parent selection.

The new *Calibrachoa* plant can be compared to plants of the male parent selection. Plants of the new *Calibrachoa* differ primarily from plants of the male parent selection in the following characteristics:

1. Plants of the new *Calibrachoa* are more compact than plants of the male parent selection.
2. Plants of the new *Calibrachoa* flower earlier than plants of the male parent selection.

Plants of the new *Calibrachoa* can be compared to plants of the *Calibrachoa* x *hybrida* 'Balcal14141', disclosed in U.S. Plant Pat. No. 30,200. In side-by-side comparisons, plants of the new *Calibrachoa* differ primarily from plants of 'Balcal14141' in the following characteristics:

1. Plants of the new *Calibrachoa* are more compact than and not as vigorous as plants of 'Balcal14141'.
2. Plants of the new *Calibrachoa* have larger flowers than plants of 'Balcal14141'.

Plants of the new *Calibrachoa* can also be compared to plants of the *Calibrachoa* spp. 'SAKCAL108', disclosed in U.S. Plant Pat. No. 24,484. In side-by-side comparisons, plants of the new *Calibrachoa* differ primarily from plants of 'SAKCAL108' in the following characteristics:

1. Plants of the new *Calibrachoa* are larger than plants of 'SAKCAL108'.
2. Plants of the new *Calibrachoa* have larger flowers than plants of 'SAKCAL108'.
3. Flowers of plants of the new *Calibrachoa* are whiter than flowers of plants of 'SAKCAL108'.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant. At the top of the photographic sheet is a side perspective view of a typical flowering plant of 'INCALCOWHI' grown in a container and at the bottom of the photographic sheet is a close-up view of a typical flowering plant of 'INCALCOWHI'.

DETAILED BOTANICAL DESCRIPTION

The aforementioned photographs and following observations and measurements describe plants grown during the spring in 15.25-cm containers in a polyethylene-covered greenhouse in St. Thomas, Ontario, Canada and under cultural practices typical of commercial *Calibrachoa* production. During the production of the plants, day temperatures averaged 27° C. and night temperatures averaged 15° C. Plants were pinched three weeks after planting and were ten weeks from planting rooted cuttings when the photographs and description were taken. In the following description, color references are made to The Royal Horticultural Society Colour Chart, 2007 Edition, except where general terms of ordinary dictionary significance are used.

Botanical classification: *Calibrachoa* sp. 'INCALCOWHI'.

Parentage:

*Female, or seed, parent*.—Proprietary selection of *Calibrachoa* Llave & Lex. identified as code number Ca14-5199-2, not patented.

*Male, or pollen, parent*.—Proprietary selection of *Calibrachoa* Llave & Lex. identified as code number Ca14-5231-6, not patented.

Propagation:

*Type*.—By vegetative terminal cuttings.

*Time to initiate roots, summer*.—About 12 days at temperatures about. 25° C.

*Time to initiate roots, winter*.—About 16 days at temperatures about 25° C.

*Time to produce a rooted plant, summer*.—About 20 days at temperatures about 25° C.

*Time to produce a rooted plant, winter*.—About 20 days at temperatures about 20° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Compact and uniformly low mounding to eventually trailing plant habit; moderately vigorous growth habit; moderate growth rate; freely branching habit with about four primary lateral branches each with about 14 secondary branches developing per plant; dense and bushy appearance.

*Plant height*.—About 11.9 cm.

*Plant diameter*.—About 25.7 cm.

Lateral branch description:

*Primary branches*.—Length: About 18.3 cm. Diameter: About 2 mm. Internode length: About 1.2 cm.

*Secondary branches*.—Length: About 9.9 cm. Diameter: About 1 mm. Internode length: About 6 mm.

*Strength*.—Moderately strong.

*Aspect*.—Initially upright then outwardly spreading to eventually trailing.

*Texture and luster*.—Moderately pubescent; matte.

*Color, developing*.—Close to 144B.

*Color, developed*.—Close to 145A.

Leaf description:

*Arrangement*.—Before flowering, alternate; after flowering, opposite; leaves simple.

*Length*.—About 3.2 cm.

*Width*.—About 1.1 cm.

*Shape*.—Elliptical.

*Apex*.—Obtuse.

*Base*.—Attenuate.

*Margin*.—Entire, not lobed.

*Texture and luster, upper surface*.—Moderately pubescent; matte.

*Texture and luster, lower surface.*—Sparsely to moderately pubescent; matte.

*Venation pattern.*—Pinnate; arcuate.

*Color.*—Developing leaves, upper and lower surfaces: Close to 147B. Fully expanded leaves, upper surface: Close to 137B; venation, close to 145A. Fully expanded leaves, lower surface: More grey than 147B; venation, close to 145B.

*Petioles.*—Length: About 2.2 mm. Diameter: About 1.6 mm. Strength: Weak to moderately strong. Texture and luster, upper and lower surfaces: Sparsely pubescent; matte. Color, upper and lower surfaces: Close to 145B.

Flower description:

*Flower type and flowering habit.*—Single salverform flowers arising from leaf axils; freely flowering habit with typically about 272 flowers and flower buds developing per plant; flowers face upright to outwardly.

*Fragrance.*—Faintly fragrant; pleasant, sweet.

*Natural flowering season.*—Early flowering, plants of the new *Calibrachoa* begin flowering about five to seven weeks after planting; plants flower continuously from the spring though the summer until frost.

*Flower longevity.*—Individual flowers last about five to seven days on the plant; flowers not persistent.

*Flower buds.*—Length: About 3.5 cm. Diameter: About 5 mm. Shape: Oblong, elongate. Texture and luster: Densely pubescent; matte. Color: Close to 144C; at the apex, close to 1D.

*Flower diameter.*—About 4.4 cm.

*Flower length (height).*—About 4.1 cm.

*Flower throat diameter.*—About 7 mm.

*Flower tube length.*—About 2.6 cm.

*Flower tube diameter.*—Proximally, about 4 mm; distally, about 8 mm.

*Corolla.*—Arrangement: Five fused petals opening into a flared trumpet. Petal lobe length (from throat): About 1.5 cm. Petal lobe width: About 1.5 cm. Petal shape: Roughly fan-shaped. Petal apex: Truncate to slightly cuspidate. Petal margin: Entire; moderately undulate. Petal texture and luster, upper surface: Smooth, glabrous, velvety; matte. Petal texture and luster, lower surface: Sparsely pubescent; matte. Throat texture and luster: Glabrous; slightly glossy. Tube texture and luster: Glabrous; matte. Color: Petal lobe, when opening, upper and lower surfaces: Close to NN155D. Petal lobe, fully opened, upper surface: Close to NN155D; venation, close to N144D; color does not change with development. Petal lobe, fully opened, lower surface: Close to NN155D; venation, close to N144A; color does not change with development. Throat: Distally, close to 157C and proximally, close to 7B; venation, close to 194B. Tube: Distally, close to 157C and proximally, close to 4C; venation, close to N144B.

*Calyx.*—Arrangement: One star-shaped calyx tube with five sepals fused towards the base and arranged in a single whorl. Sepal length: About 9 mm. Sepal width: About 3 mm. Sepal shape: Lanceolate, slightly reflexed. Sepal apex: Acute. Sepal margin: Entire. Sepal texture and luster, upper surface: Moderately pubescent; matte. Sepal texture and luster, lower surface: Sparsely to moderately pubescent; matte. Sepal color, upper surface: Close to 137B. Sepal color, lower surface: Close to 137D.

*Peduncles.*—Length: About 1.3 cm. Diameter: About 1 mm. Angle: About 45° to 90° from stem axis. Strength: Weak to moderately strong. Texture and luster: Densely pubescent; matte. Color: Close to 144A.

*Reproductive organs.*—Stamens: Quantity: Five per flower. Filament length: About 9 mm. Filament color: Close to 154C. Anther length: About 1 mm. Anther shape: Ellipsoidal. Anther color: Close to 10C. Pollen amount: Abundant. Pollen color: Close to 11B. Pistils: Quantity: One per flower. Pistil length: About 8 mm. Style length: About 7 mm. Style color: Close to 145B. Stigma diameter: Less than 1 mm. Stigma shape: Ellipsoidal. Stigma color: Close to 145A. Ovary color: Close to 145B. Seeds and fruits: To date, seed and fruit development have not been observed on plants of the new *Calibrachoa.*

Garden performance: Plants of the new *Calibrachoa* have been observed to have good garden performance and tolerate wind, rain and to be suitable for USDA Hardiness Zones 9 to 11.

Pathogen & pest resistance: Plants of the new *Calibrachoa* have not been observed to be resistant to pathogens and pests common to *Calibrachoa* plants.

It is claimed:

1. A new and distinct *Calibrachoa* plant named 'INCALCOWHI' as illustrated and described.

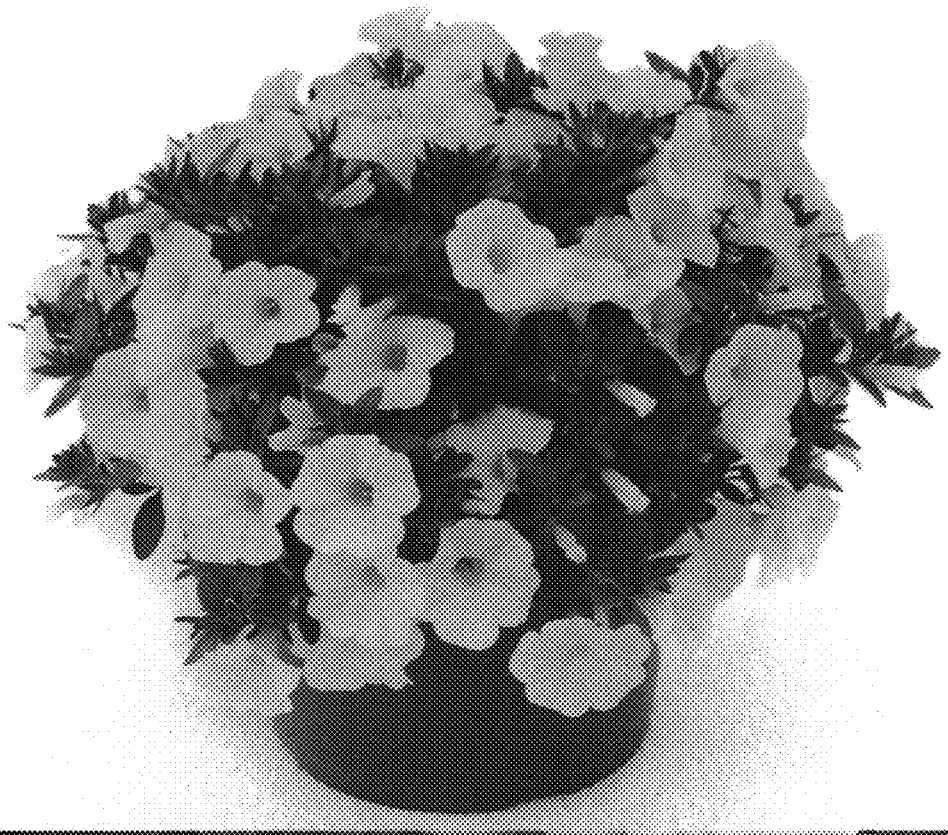
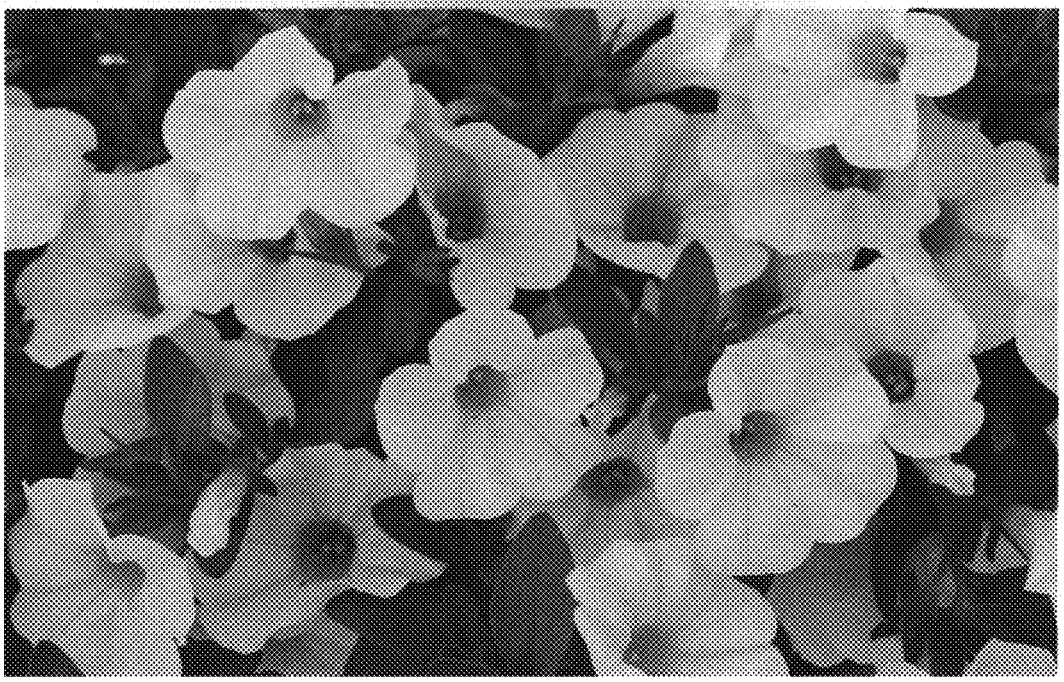

* * * * *